| United States Patent [19] | [11] 3,951,967 |
|---|---|
| Novello | [45] Apr. 20, 1976 |

[54] 7-MERCAPTO(OR THIO)-BENZOTHIADIAZINE PRODUCTS

[75] Inventor: Frederick C. Novello, Berwyn, Pa.

[73] Assignee: Merck & Co., Inc., Rahway, N.J.

[22] Filed: Dec. 4, 1974

[21] Appl. No.: 529,313

Related U.S. Application Data

[62] Division of Ser. No. 236,244, March 20, 1972, Pat. No. 3,892,738.

[52] U.S. Cl. .............................. 260/243 D; 424/246
[51] Int. Cl.² ...................................... C07D 285/22
[58] Field of Search .............................. 260/243 D

[56] References Cited
UNITED STATES PATENTS

| 3,351,595 | 11/1967 | de Stevens et al. .............. 260/243 D |
| 3,419,552 | 12/1968 | Whitehead et al. .............. 260/243 D |
| 3,514,454 | 5/1970 | McLamore et al. ............. 260/243 D |

*Primary Examiner*—Nicholas S. Rizzo
*Attorney, Agent, or Firm*—Daniel T. Szura; J. Jerome Behan

[57] ABSTRACT

7-Mercapto(or alkyl- or aralkylthio)-1,2,4-benzothiadiazine-1,1-dioxide compounds are described. Products are prepared by reducing a 7-chlorosulfonyl substituent to the 7-mercapto and then, if desired, alkylating or aralkylating to provide 7-thio substituent. Alternatively, a 4-RS-orthanilamide can be cyclized by known procedures to provide a 3-unsubstituted or 3-substituted analog. Products are xanthine oxidase inhibitors.

5 Claims, No Drawings

7-MERCAPTO(OR THIO)-BENZOTHIADIAZINE PRODUCTS

This is a division of application Ser. No. 236,244 filed Mar. 20, 1972 now U.S. Pat. No. 3,892,738 issued July 1, 1975.

This invention is concerned with benzothiadiazine compounds having a 7-mercapto or 7-thio substituent as well as methods for their preparation. The novel products of this invention have been found to exhibit marked xanthine oxidase inhibiting properties equal to or greater than exhibited by allopurinol when evaluated in the same in vitro test.

The novel products of this invention have the structural formula:

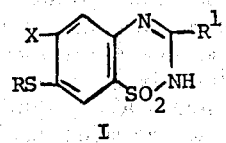

I and pharmacologically acceptable salts thereof wherein X represents halo (preferably chloro), $C_{1-3}$ alkyl (particularly methyl) and trifluoromethyl; R represents hydrogen, a straight or branched chain lower alkyl having from 1 to 6 carbon atoms and phenyl-lower alkyl having from 1 to 3 carbon atoms (preferably benzyl); $R^1$ represents hydrogen, lower alkyl having from 1 to 5 carbon atoms or substituted lower alkyl wherein the substituent is mono or dihalo (preferably chloro), and phenyl, the group $-CO_2$ lower alkyl having from 1 to 5 carbon atoms, an azine optionally substituted with one or more lower alkyl having 1 to 3 carbon atoms or a diazine optionally substituted with one or more lower alkyl having from 1 to 3 carbon atoms, or the group $-CONR^2R^3$ wherein $R^2$ and $R^3$ can be similar or dissimilar and selected from hydrogen, lower alkyl having 1 to 5 carbon atoms or hydroxy substituted lower alkyl having 1 to 5 carbon atoms.

The products of this invention can be prepared by a variety of known procedures. The methods illustrated below are representative of those employed in the preparation of the products specifically described herein:

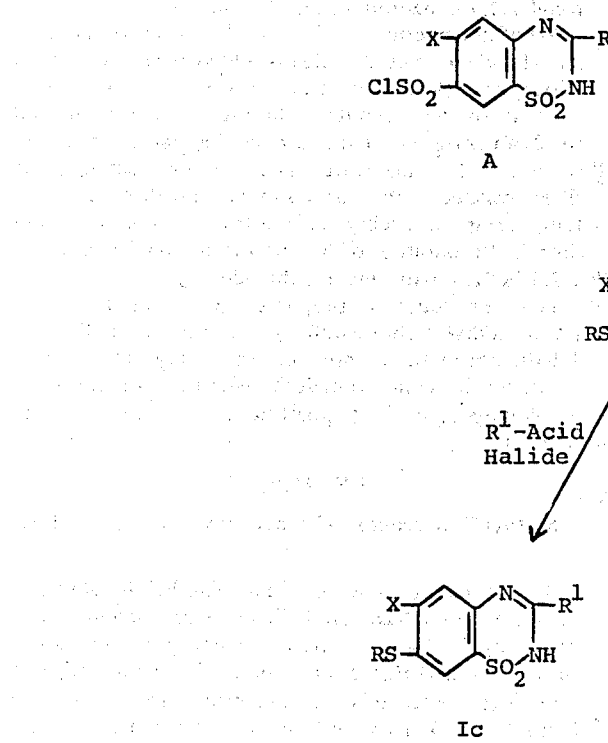
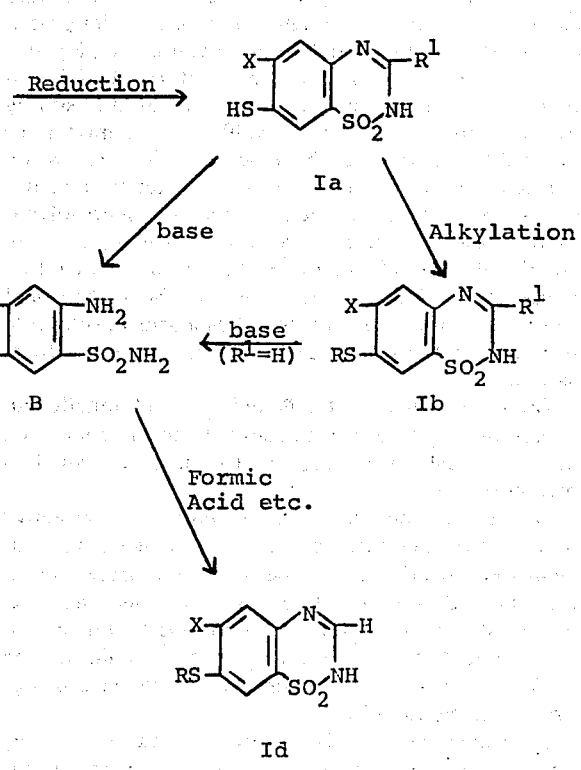

When R in structure I is hydrogen, the products can readily be prepared by reduction of the 7-chloro sulfonyl substituent of the benzothiadiazine, A. Reduction advantageously is effected with slight warming of compound A with a mixture of stannous chloride and hydrochloric acid, zinc amalgam and sulfuric acid, zinc dust and sulfuric acid or tin and hydrochloric acid. Alkylation of the 7-mercapto product, Ia, provides product Ib where R is other than hydrogen.

Slight heating of either product Ia or Ib in the presence of base provides the orthanilamide, B, which can be used to prepare compounds of this invention which are either unsubstituted in the 3-position or where certain specific substituents are desired in this position.

The appropriate orthanilamide derivative, B, can be reacted with an acid halide which, for practical purposes can be the acid chloride, followed by treatment with an organic base to provide product Ic wherein $R^1$ is other than hydrogen or a haloalkyl substituent. In the latter instance reaction with the haloalkanoic acid halide is followed by treatment with a salt of a weak acid and strong base, suitably sodium or potassium acetate or potassium fluoride.

When an organic base is employed following the reaction of the orthanilamide and acid chloride the base of choice is ammonia or a primary, secondary or tertiary amine particularly lower alkyl- or hydroxy substituted lower alkylamines. Employment of a tertiary amine in alcoholic solution provides the 3-carboxylic acid ester derivative whereas a primary or secondary amine gives the corresponding substituted amide. The 3-carbamoyl substituent is prepared employing ammonia following reaction of the orthanilamide with an alkoxalyl halide. Ammonia employed following reaction with a mono-carboxylic acid halide provides product where $R^1$ is alkyl, phenalkyl, phenyl, an azine or diazine substituent. The nature of the alkyl and halo substituents in the alkoxalyl halide is not critical and can be any lower alkyl or halide and suitable, for practical purposes, ethyl oxalyl chloride can be employed.

The $R^1$-acid chloride can be preformed and employed in the reaction or it can be prepared in situ by the addition of phosphorus oxychloride to a mixture of the orthanilamide and the $R^1$-carboxylic acid. When the acid chloride is preformed, the reaction advantageously is conducted in the presence of an inert solvent such as dioxane, tetrahydrofuran, benzene, toluene, and the like and is facilitated by heating up to the reflux temperature of the reaction mixture. When the acid chloride is formed in situ, the phosphorus oxychloride serves not only to form the acid chloride but as solvent as well.

The intermediate orthanilamide, B, additionally can be cyclized by known procedures to form product Id, advantageously by heating with formic acid or an alkyl orthoformate.

The novel products of this invention are effective inhibitors of xanthine oxidase, in decreasing the concentration of uric acid in the blood and urine and increasing the excretion of hypoxanthine and xanthine. The products are therefore useful in the treatment and management of gout preferably by oral administration of from 100 to 800 mg. per day in divided doses as prescribed by the physician.

The following examples describe various methods by which the products of this invention are prepared. It is to be understood that these examples are illustrative and not limitative of the methods or products falling within the scope of this invention.

EXAMPLE 1

6-Chloro-7-mercapto-1,2,4-benzothiadiazine-1,1-dioxide

A solution of stannous chloride dihydrate (180.5 g., 0.80 mole) in concentrated hydrochloric acid (160 ml.) is added to a stirred solution of 6-chloro-7-chlorosulfonyl-1,2,4-benzothiadiazine-1,1-dioxide (50.4 g., 0.16 mole) at 75° C. and maintained at this temperature for an additional 20–30 minutes. The solution is concentrated in vacuo to one-tenth its original volume and poured into 8 liters of ice water containing concentrated hydrochloric acid (200 ml.). The solid formed is collected and added with stirring to one liter of saturated sodium bicarbonate solution. After one hour, the solution is filtered and the filtrate acidified with hydrochloric acid, the product collected on a filter, washed with water and recrystallized from ethanol providing product melting at 270°–272° C.

Analysis calculated for $C_7H_5ClN_2O_2S_2$:
C, 33.80; H, 2.03; N, 11.26;
Found: C, 34.24; H, 2.14; N, 11.26.

By replacing the stannous chloride and concentrated hydrochloric acid employed in the above example by zinc amalgam and sulfuric acid, zinc dust and sulfuric acid, or tin and concentrated hydrochloric acid the same product is obtained.

EXAMPLE 2

6-Trifluoromethyl-7-mercapto-1,2,4-benzothiadiazine-1,1-dioxide

Step A: Preparation of 6-Trifluoromethyl-7-chlorosulfonyl-1,2,4-benzothiadiazine-1,1-dioxide 6-Trifluoromethyl-7-sulfamoyl-1,2,4-benzothiadiazine-1,1-dioxide (0.2 mole) is added portionwise with stirring to chlorosulfonic acid (300 ml.) cooled in an ice-bath over 30 minutes. The mixture is then heated for 2 hours on the steam bath, cooled and poured onto a mixture of ice and water. The solid is collected on the filter, washed with cold water and air-dried at room temperature and recrystallized from acetone-hexane.

Step B: Preparation of 6-Trifluoromethyl-7-mercapto-1,2,4-benzothiadiazine-1,1-dioxide This product is prepared by reducing 6-trifluoromethyl-7-chlorosulfonyl-1,2,4-benzothiadiazine-1,1-dioxide with stannous chloride dihydrate by substantially the same procedure described in Example 1, employing equivalent quantities of all reactants and reagents.

EXAMPLE 3

6-Methyl-7-mercapto-1,2,4-benzothiadiazine-1,1-dioxide

By replacing the 6-trifluoromethyl-7-sulfamoyl-1,2,4-benzothiadiazine-1,1-dioxide employed in Step A of Example 1 by an equivalent quantity of 6-methyl-7-sulfamoyl-1,2,4-benzothiadiazine-1,1-dioxide and then following substantially the same procedure described in Steps A and B of Example 1, there is obtained 6-methyl-7-mercapto-1,2,4-benzothiadiazine-1,1-dioxide.

EXAMPLE 4

6-Chloro-7-isopropylthio-1,2,4-benzothiadiazine-1,1-dioxide

A suspension of 6-chloro-7-mercapto-1,2,4-benzothiadiazine-1,1-dioxide (49.7 g., 0.02 mole), prepared as described in Example 1, in dimethylformamide (300 ml.) is heated with anhydrous potassium carbonate (27.6 g., 0.02 mole) with stirring. A solution results within 30 minutes whereupon isopropyl chloride (0.022 mole) is added with stirring over a 30-minute period. The reaction mixture is heated on a steam bath for one hour, poured onto a mixture of ice (2 liters) and water (2 liters) and acidified with concentrated hydrochloric acid. The solid is collected, stirred with 5% sodium hydroxide solution (1500 ml.) at room temperature and filtered. The filtrate is acidified with concentrated hydrochloric acid and the product collected and recrystallized from a mixture of methanol and water to provide 6-chloro-7-isopropylthio-1,2,4-benzothiadiazine-1,1-dioxide, m.p. 231°–232° C.

Analysis calculated for $C_{10}H_{11}ClN_2O_2S_2$:
C, 41.30; H, 3.81; N, 9.64;
Found: C, 41.48; H, 3.88; N, 9.65.

Following the procedure of Example 4 but replacing the isopropyl chloride by an equivalent quantity of benzyl chloride, n-propyl chloride and 1-ethylpropyl chloride, respectively, there is obtained

EXAMPLE 5

6-Chloro-7-benzylthio-1,2,4-benzothiadiazine-1,1-dioxide, m.p. 268°–271° C.

Analysis calculated for $C_{14}H_{11}ClN_2O_2S_2$:
C, 49.62; H, 3.27; N, 8.27;
Found: C, 50.14; H, 3.43; N, 8.24.

EXAMPLE 6

6-Chloro-7-n-propylthio-1,2,4-benzothiadiazine-1,1-dioxide, m.p. 193°–194° C.

Analysis calculated for $C_{10}H_{11}ClN_2O_2S_2$:
C, 41.30; H, 3.81; N, 9.64;
Found: C, 41.55; H, 3.87; N, 9.72.

EXAMPLE 7

6-Chloro-7-(1-ethylpropylthio)-1,2,4-benzothiadiazine-1,1-dioxide, m.p. 208°–209° C.

Analysis calculated for $C_{12}H_{15}ClN_2O_2S_2$:
C, 45.20; H, 4.74; N, 8.79;
Found: C, 45.32; H, 4.54; N, 8.83.

The products identified in Table I are prepared by the process of Example 4 employing equivalent quantities of the benzothiadiazine and the alkyl chloride (R-Cl) identified in the table.

TABLE I

| Ex. No. | X | R |
|---|---|---|
| 8 | $CF_3$ | $(CH_3)_2$—CH— |
| 9 | $CH_3$ | $(CH_3)_2$—CH— |
| 10 | $CF_3$ | $CH_3(CH_2)_2$— |
| 11 | $CH_3$ | $CH_3(CH_2)_2$— |
| 12 | $CH_3$ | $(C_2H_5)_2$—CH— |

EXAMPLE 13

3-(pyrid-4-yl)-6-chloro-7-isopropylthio-1,2,4-benzothiadiazine-1,1-dioxide

Step A-1: Preparation of 2-sulfamoyl-4-isopropylthio-5-chloroaniline

6-Chloro-7-isopropylthio-1,2,4-benzothiadiazine-1,1-dioxide (0.03 mole), prepared as described in Example 2, is dissolved in 10 percent aqueous sodium hydroxide (50 ml.) and heated on the steam bath for one hour. The solution is chilled, acidified with hydrochloric acid and the product upon recrystallization from a mixture of ethanol and water melts at 137°–138° C.

Analysis calculated for $C_9H_{13}ClN_2O_2S_2$:
C, 38.50; H, 4.66; N, 9.98;
Found: C, 38.71; H, 4.60; N, 9.81.

Step A-2: Preparation of 2-sulfamoyl-4-n-propylthio-5-chloroaniline

By replacing the 1,2,4-benzothiadiazine derivative employed in Step A-1 by an equivalent quantity of 6-chloro-7-n-propylthio-1,2,4-benzothiadiazine-1,1-dioxide, prepared as described in Example 4, and following substantially the same procedure described in Step A-1 there is obtained 2-sulfamoyl-4-n-propylthio-5-chloroaniline, m.p. 109°–111° C.

Analysis calculated for $C_9H_{13}ClN_2O_2S_2$:
C, 38.50; H, 4.66; N, 9.98;
Found: C, 38.14; H, 4.57; N, 9.83.

Step A-3: Preparation of 2-sulfamoyl-4-mercapto-5-chloroaniline

By replacing the 1,2,4-benzothiadiazine derivative employed in Step A-1 by an equivalent quantity of 6-chloro-7-mercapto-1,2,4-benzothiadiazine-1,1-dioxide and following substantially the same procedure described in Step A-1 there is obtained 2-sulfamoyl-4-mercapto-5-chloroaniline, m.p. 192°–195° C.

Analysis calculated for $C_6H_7ClN_2O_2S_2$:
C, 30.18; H, 2.96; N, 11.74;
Found: C, 30.50; H, 3.20; N, 11.74.

Step A-4: Preparation of 2-sulfamoyl-4-(1-ethylpropylthio)-5-chloroaniline

By replacing the 1,2,4-benzothiadiazine derivative employed in Step A-1 by an equivalent quantity of 6-chloro-7-(1-ethylpropylthio)-1,2,4-benzothiadiazine-1,1-dioxide (prepared as described in Example 7) and following substantially the same procedure described in Step A-1, there is obtained 2-sulfamoyl-4-(1-ethylpropylthio)-5-chloroaniline, m.p. 118°–120° C.

Analysis calculated for $C_{11}H_{17}ClN_2O_2S_2$:
C, 42.78; H, 5.55; N, 9.07;
Found: C, 42.58; H, 5.41; N, 9.09.

In like manner the following compounds of Step A-5 to Step A-9 are prepared by replacing the benzothiadiazine derivative employed in Step A-1 by an equivalent quantity of 6-trifluoromethyl-7-isopropylthio-1,2,4-benzo-
thiadiazine-1,1-dioxide (Ex. 8 product)
6-methyl-7-isopropylthio-1,2,4-benzothiadiazine-
1,1-dioxide (Ex. 9 product)
6-trifluoromethyl-7-n-propylthio-1,2,4-benzothiadia-
zine-1,1-dioxide (Ex. 10 product)
6-methyl-7-n-propylthio-1,2,4-benzothiadiazine-1,1-
dioxide (Ex. 11 product)
6-methyl-7-(1-ethylpropylthio)-1,2,4-benzothiadia-
zine-1,1-dioxide (Ex. 12 product)
and following substantially the same procedure de-
scribed in
Step A-1, providing respectively:
Step A-5: 2-sulfamoyl-4-isopropylthio-5-trifluorome-
thylaniline,
Step A-6: 2-sulfamoyl-4-isopropylthio-5-methylaniline,
Step A-7: 2-sulfamoyl-4-n-propylthio-5-trifluorome-
thylaniline,
Step A-8: 2-sulfamoyl-4-n-propylthio-5-methylaniline, and
Step A-9: 2-sulfamoyl-4-(1-ethylpropylthio)-5-methylaniline.
Step B: Preparation of 3-(pyrid-4-yl)-6-chloro-7-iso-
propylthio-1,2,4-benzothiadiazine-1,1-dioxide An intimate mixture of the orthanilamide derivative prepared as described in Step A-1 (0.01 mole) and 4-pyridine carboxylic acid (0.01 mole) is heated with 20 ml. of phosphorus oxychloride for 15 minutes at 50° C. and 45 minutes on the steam bath. The solution is cooled, poured onto ice and the product heated on the steam bath with ethanol (50 ml.) and concentrated ammonium hydroxide (50 ml.) for 2 hours. After concentration in vacuo, the residue is treated with 50 ml. of water acidified with hydrochloric acid yielding 3-(pyrid-4-yl)-6-chloro-7-isopropylthio-1,2,4-benzo-thiadiazine-1,1-dioxide which following recrystallization from a mixture of dimethylformamide and water, melts at 254°–256° C.

Analysis calculated for $C_{15}H_{14}ClN_3O_2S_2$:
C, 48.97; H, 3.84; N, 11.42;
Found: C, 49.14; H, 3.82; N, 11.42.

The products identified in Table II are made by the process described in Example 13, Step B, except that the orthanilamide and the 4-pyridine carboxylic acid are replaced by the orthanilamide and heterocyclic carboxylic acid identified in the table. The R and R" groups in the reactants are retained unchanged in the end product, I-c.

TABLE II

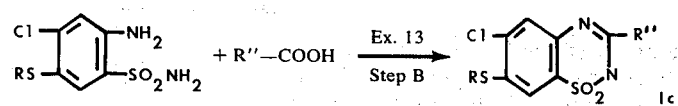

| Ex. No. | R | R" | m.p.°C | Formula | Calculated C | H | N | Found C | H | N |
|---|---|---|---|---|---|---|---|---|---|---|
| 14 | i-propyl | pyrimidin-yl | 225–26 | $C_{14}H_{13}ClN_4O_2S_2$ | 45.58 | 3.55 | 15.19 | 45.63 | 3.58 | 15.04 |
| 15 | n-propyl | pyrid-4-yl | 284–86 | $C_{15}H_{14}ClN_3O_2S_2$ | 48.97 | 3.84 | 11.42 | 48.54 | 3.53 | 11.13 |
| 16 | n-propyl | pyridazin-yl | 279–81 | $C_{14}H_{13}ClN_4O_2S_2$ | 45.58 | 3.55 | 15.19 | 45.49 | 3.63 | 15.29 |
| 17 | n-propyl | pyrimidin-yl | 248–50 | $C_{14}H_{13}ClN_4O_2S_2$ | 45.58 | 3.55 | 15.19 | 45.85 | 3.69 | 14.89 |
| 18 | n-propyl | methylpyrimidinyl | 248–50 | $C_{15}H_{15}ClN_4O_2S_2$ | 47.05 | 3.95 | 14.63 | 47.05 | 3.95 | 14.62 |
| 19 | n-propyl | methylpyrimidinyl | 254–56 | $C_{15}H_{15}ClN_4O_2S_2$ | 47.05 | 3.95 | 14.63 | 46.84 | 3.91 | 14.64 |
| 20 | n-propyl | pyrazin-yl | 310–12 | $C_{14}H_{13}ClN_4O_2S_2$ | 45.58 | 3.55 | 15.19 | 45.51 | 3.46 | 15.02 |

Additional products I-c that are made by the procedure described in Example 13, Step B, by employing equivalent quantities of the orthanilamide and R''-COOH are identified in Table III:

Analysis calculated for $C_8H_7ClN_2O_2S_2$:
C, 36.57; H, 2.69; N, 10.66;
Found: C, 36.98; H, 2.73; N, 10.61.

TABLE III $$X\text{-}\underset{RS}{\overset{NH_2}{\bigcirc}}\text{-}SO_2NH_2 + R''\text{-}COOH \xrightarrow[\text{Step B}]{\text{Ex. 13}} X\text{-}\underset{RS}{\overset{N}{\bigcirc}}\text{-}\underset{SO_2}{\overset{N}{\diagdown}}R''$$

I-c

| Ex. No. | X | R | R'' |
|---|---|---|---|
| 21 | —CF$_3$ | i-propyl | 4-pyridyl |
| 22 | —CH$_3$ | i-propyl | 4-pyridyl |
| 23 | —CF$_3$ | n-propyl | 4-pyridyl |
| 24 | —CH$_3$ | n-propyl | 4-pyridyl |
| 25 | —CF$_3$ | i-propyl | pyrazinyl |
| 26 | —CF$_3$ | i-propyl | pyrimidinyl |

EXAMPLE 27

3-Methyl-6-chloro-7-mercapto-1,2,4-benzothiadiazine-1,1-dioxide

A mixture of 2-sulfamoyl-4-mercapto-5-chloroaniline, prepared as described in Example 13, Step A-3 (0.02 mole) and acetyl chloride (0.022 mole) in 75 ml. of dioxane is heated under reflux for 24 hours. The solution is concentrated to dryness in vacuo and the residue dissolved in 75 ml. of ethanol and treated with 75 ml. of concentrated ammonium hydroxide in the cold. Thereafter the solution is heated under reflux for three hours and concentrated to dryness in vacuo. The residue is suspended in 100 ml. of water acidified with hydrochloric acid and the product, following recrystallization from dimethylformamide-water, melts at 304°–305° C.

EXAMPLE 28

3-Ethoxycarbonyl-6-trifluoromethyl-7-isopropylthio-1,2,4-benzothiadiazine-1,1-dioxide This product is prepared by replacing the orthanilamide, the acetyl chloride and the ammonium hydroxide employed in Example 27 by equivalent quantities of 2-sulfamoyl-4-isopropylthio-5-trifluoromethylaniline, ethyl oxalyl chloride and trimethylamine, respectively and otherwise following substantially the same procedure described in Example 27.

The products identified in Table IV are prepared following substantially the same procedure described in Example 27 but replacing the orthanilamide derivative, the acid chloride, and ammonium hydroxide by the reactants and reagents identified in the following table:

TABLE IV $$Cl\text{-}\underset{RS}{\overset{NH_2}{\bigcirc}}\text{-}SO_2NH_2 + R''\text{-}COCl \xrightarrow[\text{Ex. 27}]{\text{base}} Cl\text{-}\underset{RS}{\overset{N}{\bigcirc}}\text{-}\underset{SO_2}{\overset{N}{\diagdown}}R'$$

| Ex. No. | R | R'' | base | m.p.°C | Formula | Calculated C | H | N | Found C | H | N |
|---|---|---|---|---|---|---|---|---|---|---|---|
| 29 | H | C$_6$H$_5$CH$_2$— | NH$_4$OH | > 300 | C$_{14}$H$_{11}$ClN$_2$O$_2$S$_2$ | 49.62 | 3.27 | 8.26 | 49.96 | 3.01 | 8.31 |
| 30 | i-propyl | C$_2$H$_5$O$_2$C— | (CH$_3$)$_3$N | 258–60 | C$_{13}$H$_{15}$ClN$_2$O$_4$S$_2$ | 43.03 | 4.17 | 7.72 | 43.12 | 4.21 | 7.71 |
| 31 | i-propyl | (CH$_3$)$_2$NOC— | (CH$_3$)$_2$NH | 212–14 | C$_{13}$H$_{16}$ClN$_3$O$_3$S$_2$ | 43.15 | 4.46 | 11.61 | 43.28 | 4.44 | 11.60 |
| 32 | i-propyl | CH$_3$HNOC— | CH$_3$NH$_2$ | 323–25 | C$_{12}$H$_{14}$ClN$_3$O$_3$S$_2$ | 41.43 | 4.06 | 12.08 | 41.78 | 3.92 | 11.97 |
| 33 | n-propyl | HO(CH$_2$)$_2$HNOC— | NH$_2$(CH$_2$)$_2$OH plus dioxane | 277–79 | C$_{13}$H$_{16}$ClN$_3$O$_4$S$_2$ | 41.32 | 4.27 | 11.12 | 41.32 | 4.14 | 11.09 |

EXAMPLE 34

3-Carbamoyl-6-chloro-7-isopropylthio-1,2,4-benzothiadiazine-1,1-dioxide

A mixture of 2-sulfamoyl-4-isopropylthio-5-chloroaniline (0.02 mole) and ethyl oxalyl chloride (0.022 mole) in dioxane (40 ml.) is heated under reflux for 18 hours and then concentrated to dryness in vacuo. The residue is dissolved in a mixture of ethanol (30 ml.) and concentrated ammonium hydroxide (30 ml.) and stirred at room temperature for 2–3 days. The solution is concentrated to dryness in vacuo and the residue stirred in sodium bicarbonate solution and filtered. The filtrate is acidified and the product recrystallized from dimethylformamide-water providing 3-carbamoyl-6-chloro-7-isopropylthio-1,2,4-benzothiadiazine-1,1-dioxide, m.p. 279°–280° C.

Analysis calculated for $C_{11}H_{12}ClN_3O_3S_2$:
C, 39.58; H, 3.62; N, 12.59;
Found: C, 39.41; H, 3.77; N, 12.62.

EXAMPLE 35

3-Carbamoyl-6-chloro-7-(1-ethylpropylthio)-1,2,4-benzothiadiazine-1,1-dioxide By replacing the orthanilamide employed in Example 34 by an equimolecular quantity of 2-sulfamoyl-4-(1-ethylpropylthio)-5-chloroaniline and following substantially the same procedure described in Example 34 there is obtained 3-carbamoyl-6-chloro-7-(1-ethylpropylthio)1,2,4-benzothiadiazine-1,1-dioxide, m.p. 287°–289° C.

Analysis calculated for $C_{13}H_{16}ClN_3O_3S_2$:
C, 43.15; H, 4.46; N, 11.61;
Found: C, 43.18; H, 4.38; N, 11.63.

EXAMPLE 36

3-Chloromethyl-6-chloro-7-isopropylthio-1,2,4-benzothiadiazine-1,1-dioxide

A mixture of 2-sulfamoyl-4-isopropylthio-5-chloroaniline (0.02 mole) and chloroacetyl chloride (0.022 mole) in dioxane (75 ml.) is heated under reflux for 24 hours. The solution then is concentrated to dryness in vacuo, the residue dissolved in ethanol (60 ml.) and heated under reflux with potassium acetate (0.022 mole) and water (10 ml.) for 2 hours. The alcohol is removed in vacuo and the solution then acidified with hydrochloric acid. The precipitated product is recrystallized from a mixture of methanol and water to provide 3-chloromethyl-6-chloro-7-isopropylthio-1,2,4-benzothiadiazine-1,1-dioxide, m.p. 248°–250° C.

Analysis calculated for $C_{11}H_{12}Cl_2N_2O_2S_2$:
C, 38.94; H, 3.57; N, 8.26;
Found: C, 39.16; H, 3.65; N, 8.28.

EXAMPLE 37

3-Chloromethyl-6-trifluoromethyl-7-isopropylthio-1,2,4-benzothiadiazine-1,1-dioxide This product is prepared following substantially the same procedure described in Example 36 with the exception that an equivalent quantity of 2-sulfamoyl-4-isopropylthio-5-trifluoromethylaniline is employed in place of the aniline reactant used in Example 36.

Example 38

3-Chloromethyl-6-chloro-7-(1-ethylpropylthio)-1,2,4-benzothiadiazine-1,1-dioxide By replacing the orthanilamide employed in Example 36 by an equimolecular quantity of 2-sulfamoyl-4-(1-ethylpropylthio)-5-chloroaniline and following substantially the same procedure described in Example 36 there is obtained 3-chloromethyl-6-chloro-7-(1-ethylpropylthio)-1,2,4-benzothiadiazine-1,1-dioxide, m.p. 213°–214° C.

Analysis calculated for $C_{13}H_{16}Cl_2N_2O_2S_2$:
C, 42.51; H, 4.39; N, 7.63;
Found: C, 43.05; H, 4.56; N, 7.63

EXAMPLE 39

3-Chloromethyl-6-methyl-7-(1-ethylpropylthio)-1,2,4-benzothiadiazine-1,1-dioxide This product is prepared following substantially the same procedure described in Example 36 except that an equivalent quantity of 2-sulfamoyl-4-(1-ethylpropylthio)-5-methylaniline is substituted for the aniline reactant employed in Example 36.

EXAMPLE 40

3-Dichloromethyl-6-chloro-7-isopropylthio-1,2,4-benzothiadiazine-1,1-dioxide By replacing the acid chloride employed in Example 36 by an equimolecular quantity of dichloroacetyl chloride and following substantially the same procedure described in Example 36 there is obtained 3-dichloromethyl-6-chloro-7-isopropylthio-1,2,4-benzothiadiazine-1,1-dioxide, m.p. 287°–289° C.

Analysis calculated for $C_{11}H_{11}Cl_3N_2O_2S_2$:
C, 35.35; H, 2.97; N, 7.50;
Found: C, 35.41; H, 3.11; N, 7.54.

What is claimed is:

1. A 3-$R^1$-6-X-7-RS-1,2,4-benzothiadiazine-1,1-dioxide and pharmacologically acceptable salts thereof wherein X represents $C_{1-3}$-alkyl, chloro and trifluoromethyl; $R^1$ represents pyrazinyl, lower alkyl substituted pyrazinyl, pyridazinyl, lower alkyl substituted pyridazinyl, pyrimidinyl and lower alkyl substituted pyrimidinyl, and R represents hydrogen, lower alkyl and phenyl-lower alkyl.
2. A product as claimed in claim 1 wherein X is trifluoromethyl and $R^1$ represents pyrazinyl, pyridazinyl and pyrimidinyl.
3. A product as claimed in claim 1 wherein X is chloro, and $R^1$ is an unsubstituted diazine.
4. A product as claimed in claim 1 wherein X is chloro, R is isopropyl and $R^1$ is 4-pyridazinyl.
5. A product as claimed in claim 1 wherein X is chloro, R is isopropyl and $R^1$ is 4-pyrimidinyl.

* * * * *